United States Patent
Lieberman

(10) Patent No.: US 6,837,905 B1
(45) Date of Patent: Jan. 4, 2005

(54) SPINAL VERTEBRAL FUSION IMPLANT AND METHOD

(76) Inventor: Daniel M. Lieberman, 7548 N. 22nd St., Phoenix, AZ (US) 85020

(*) Notice: Subject to any disclaimer, the term of this patent is extended or adjusted under 35 U.S.C. 154(b) by 0 days.

(21) Appl. No.: 10/257,000

(22) Filed: Sep. 26, 2002

(51) Int. Cl.⁷ .............................. A61F 2/44; A61F 5/00
(52) U.S. Cl. ...................................... 623/17.16; 606/61
(58) Field of Search ................. 623/17.11, 17.12, 623/17.13, 17.14, 17.15, 17.16; 606/60, 61, 62, 65, 69, 71, 72, 73

(56) References Cited

U.S. PATENT DOCUMENTS

| | | | | |
|---|---|---|---|---|
| 4,955,908 A | * | 9/1990 | Frey et al. ............... | 623/17.16 |
| 5,092,893 A | * | 3/1992 | Smith ..................... | 606/61 |
| 5,344,421 A | * | 9/1994 | Crook ..................... | 606/61 |
| 5,674,296 A | * | 10/1997 | Bryan et al. ............. | 623/17.16 |
| 5,681,311 A | * | 10/1997 | Foley et al. ............. | 606/61 |
| 5,916,267 A | * | 6/1999 | Tienboon ................. | 623/17.11 |
| 6,106,557 A | * | 8/2000 | Robioneck et al. ........ | 623/17.15 |
| 6,190,413 B1 | * | 2/2001 | Sutcliffe ................. | 623/17.11 |
| 6,203,573 B1 | * | 3/2001 | Walter et al. ............ | 623/16.11 |
| 6,224,630 B1 | * | 5/2001 | Bao et al. ............... | 623/17.16 |
| 6,235,059 B1 | * | 5/2001 | Benezech et al. ......... | 623/17.16 |
| 6,306,136 B1 | * | 10/2001 | Baccelli ................... | 606/61 |
| 6,562,073 B2 | * | 5/2003 | Foley ..................... | 623/17.11 |

* cited by examiner

*Primary Examiner*—David J. Isabella
(74) *Attorney, Agent, or Firm*—Gregory J. Nelson

(57) ABSTRACT

An implant and method for fusion of adjacent vertebra. The implant has a curved plate having bores for reception of bone screws. In one embodiment, aligned medial sots extend longitudinally in the plate. An interbody graft is attached to or is integrally formed with the plate. In use, retraction post are temporarily secured to adjacent vertebrae and the slots aligned with posts. The graft is inserted and adjacent vertebrae are compressed and held until permanent screw fixation is completed. The compression tool and the posts are removed leaving the vertebrae compressed against the graft to promote healing. In an alternate embodiment, the plate carries multiple grafts which are slidably relative to the plate.

16 Claims, 3 Drawing Sheets

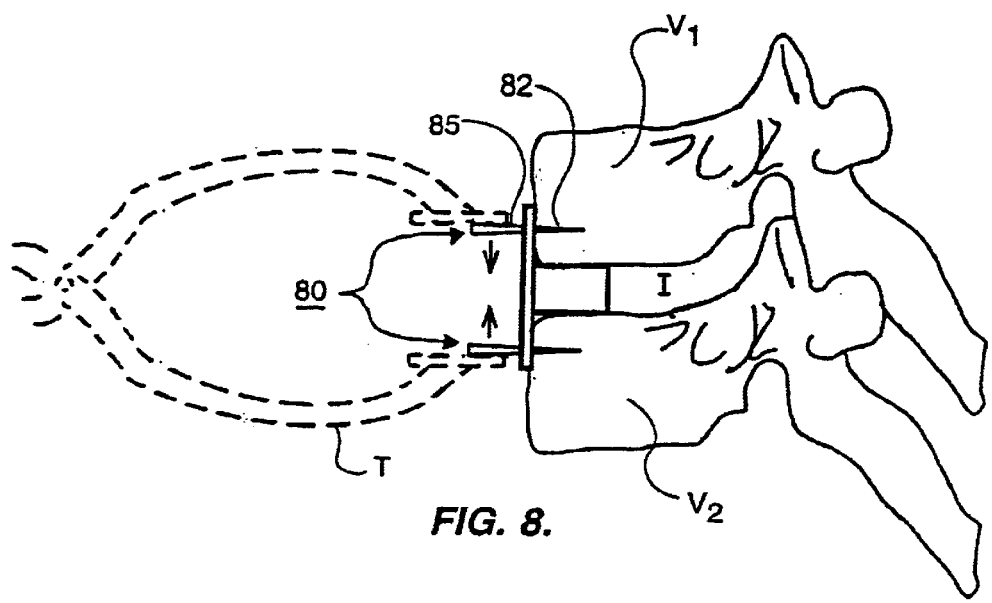
FIG. 8.
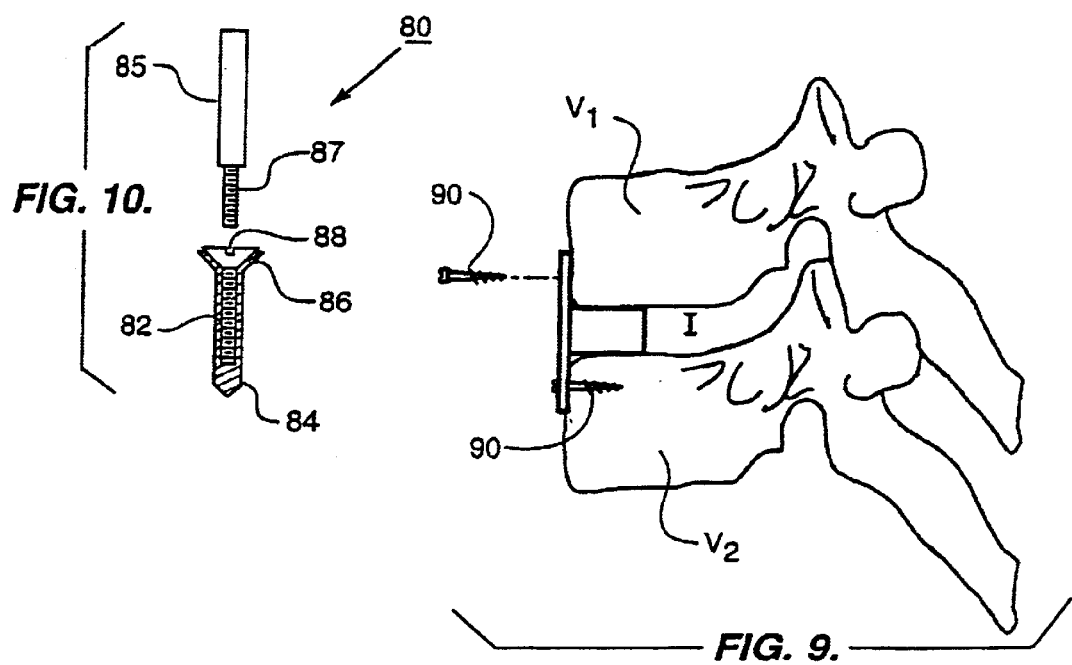
FIG. 10.
FIG. 9.

SPINAL VERTEBRAL FUSION IMPLANT AND METHOD

FIELD OF THE INVENTION

The present invention relates to an implant for facilitating fusion of adjacent bone structures and more particularly relates to a graft and surgical method for fusing adjacent vertebrae.

BACKGROUND OF THE INVENTION

The spine consists of a series of bone structures termed "vertebrae." Between each vertebra are strong connective tissues termed "discs" which hold one vertebra to another and which also act as a cushion between the vertebrae. The discs are flexible material which absorb shock forces associated with movement. The spine has different sections including the cervical or neck portion, the thoracic chest area and the lumbar lower back or lumbar section. Fusion is a surgical technique in which one or more of the vertebrae of the spine are united or joined to prevent relative movement. The spinal fusion procedure does not directly connect the vertebrae, rather a bone graft is positioned between adjacent vertebrae interbody graft of the spine during surgery. Over a period of time healing occurs as living bone from vertebrae span the interbody graft secures the adjacent vertebrae together. Fusion has occurred when living bone has completely spanned the graft and the adjacent vertebrae are thus connected by a solid bridge of bone.

In the neck, compression of cervical nerve roots by extruded discs or bone spurs is common. Symptoms may include pain, numbness, weakness and disordered reflex symptoms due to compression of a nerve root are called radiculopathy. Cervical radiculopathies are generally treated by resection of the discs or bones utilizing a surgical approach from the front or anterior aspect to the neck. Once the anterior cervical discectomy is completed, common procedure is to place a bone graft between the vertebral bodies in place of the removed disc. Other conditions which may require fusion include treatment of fractured or broken vertebrae, correction of deformities or treatment of instability.

Traditionally, interbody grafts are fashioned from bone taken from a patient's skeleton, termed an "autograft." Most grafts are now harvested from a cadaver, termed "alografts." Interbody grafts may also be formed from synthetic materials such as titanium, carbon fiber and plastics. Since harvesting of an autograft is painful, many surgeons prefer the use of alografts. However, alografts are associated with a relatively high rate of dislodgement due to the patient's neck movement during the healing process. To minimize the risk of dislodgement of the interbody graft posteriorly toward the spinal cord, surgeons routinely mortise the graft by drilling a shelf into the vertebrae. To minimize the risk of dislodgement of the interbody graft anteriorly towards the esophagus, surgeons routinely place a metal plate across the inner space and secure it with screws extending into the vertebrae.

Placement of an anterior cervical plate with a screw fixation effectively prevents interbody graft dislodgement toward the esophagus and enhances fusion by providing rigid fixation between the vertebrae. However, this procedure has several disadvantages. In the natural healing process, bone growth and replacement is stimulated by application of force (Wolf's Law). Placement of anterior cervical instrumentation removes forces applied to the neck, potentially lessening replacement bone growth. In addition, if the anterior cervical plate is rigid, it tends to redistribute force asymmetrically to the vertebrae above and below those undergoing fusion. Creation of an unbalanced force may accelerate wear and degenerative changes at the levels adjacent the fusion. Another disadvantage associated with interbody grafts is the loss of vertebral body bone required to create a mortise. Since a typical vertebrae is about 20 mm thick, the creation of a 2 mm mortise results in a loss of approximately 10% of the bone mass available for fusion and requires a fusion mass of greater length to fill the opening created by the dissectomy.

Accordingly, there exists a need for an improved anterior cervical graft and procudure which will eliminate the need to mortise the graft and which will allow compression to facilitate healing and fusion.

BRIEF OF SUMMARY OF THE INVENTION

Briefly, the present invention relates to an implant and method for facilitating fusion of adjacent vertebrae. The implant has a cervical plate which is rigid and is preferably curved along its longitudinal axis to generally conform to the natural lordotic curve of the cervical spine. The plate may be constructed from metal, a composite material such as carbon fiber or medically acceptable, bioabsorbable plastics such as polylactic acid (PLA) and polyglycolic acid (PGA). The plate has a pair of upper and lower bores for reception of screws for permanent fixation to the adjacent vertebrae. In one embodiment having a single graft, aligned medial slots extend longitudinal in the plate. The interbody graft is secured to the center of a plate and may be mechanically secured to the plate or adhesively secured. The graft may be an alograft, autograft or synthetic graft.

The entire plate and graft may also be integrally formed, as by molding, from bioabsorbable materials. If multiple vertebral segments are to be fused, the plate is increased in size to extend the necessary length along the spine and is provided with slidable grafts which may be axially positioned to align with the intervertebral space, as well as additional bores and medial slots.

When inserting the plate of FIGS. 1 to 4, retraction posts are temporarily secured to adjacent vertebrae and the plate positioned so that the medial slots align with the posts and the graft aligns with the vertebral area. The graft is then inserted between the vertebrae and the adjacent vertebrae are compressed using a tool to apply force to the posts. While in the compressed position, locking bone screws are inserted through the bores in the plate and into the bone to permanently affix the plate to the vertebrae in the compressed position. Once the bone screws are in place, the compression tool and the temporary posts are removed and the graft remains compressed in the intervertebral space to promote healing.

The implant carrying multiple grafts, as seen in FIGS. 5 to 7, is surgically implanted in generally the same manner with the medial slot receiving the temporary retraction posts and also allowing the grafts to be axially positioned to align with the proper intervertebral space.

BRIEF DESCRIPTION OF THE DRAWINGS

The above and other objects and advantages of the present invention will become more apparent from the following description, claims and drawings in which:

FIGS. 8 and 9 illustrate the implant procedure using the implant of the present invention; and FIG. 10 shows the retraction compression posts used in the fusion procedure.

DETAILED DESCRIPTION OF THE DRAWINGS

Figure 1:
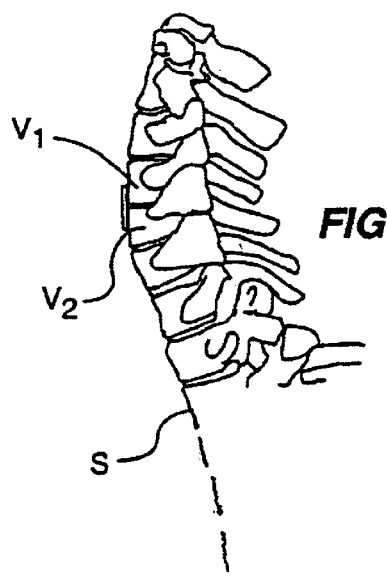
FIG. 1 is a lateral view of a representative vertebral column.

Referring now to FIG. 1, a representative spinal column S is shown. The spinal column S is comprised of a series of bone structures called vertebrae. Between each vertebrae are discs consisting of strong connective tissue which hold the vertebrae together and act as a cushion. The fusion implant of the present invention may be inserted at various locations along the spine including the cervical, thoracic or lumbar section. For purposes of description, the implant 10 is shown as being anteriorly inserted in an intermediate location in the cervical spine between vertebrae designated V1 and V2. Generally with a procedure of this type, the disc material between the vertebrae V1 and V2 is first removed and an implant termed a "graft" is placed between the vertebrae to fixate the vertebrae and serve as a scaffold for bone growth leading to fusion. With the present invention, the inserted graft remains subject to compression to promote healing and fusion.

Figure 2:
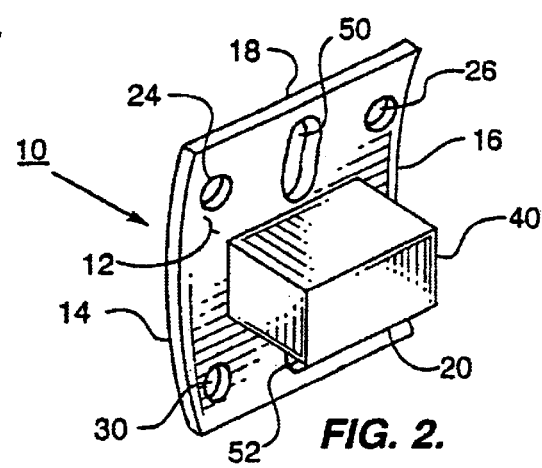
FIG. 2 is a perspective view of spinal fusion implant according to one embodiment the present invention.
Figure 3:
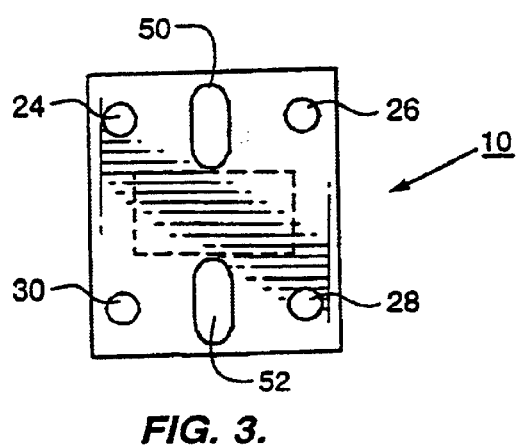
FIG. 3 is a front view thereof.
Figure 4:
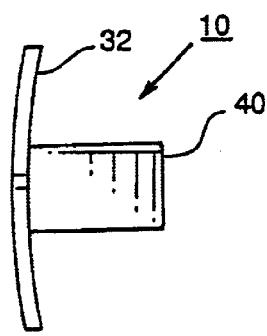
FIG. 4 is a side view thereof.

Turning now to the drawings, particularly FIGS. 2 to 4, the implant 10 includes a base member which is shown as a plate 12 which may be generally rectangular. The plate has opposite side edges 14 and 16, and top and bottom edges 18 and 20. The dimensions of the plate may vary depending upon the physical requirement, but for most adult fusion applications on a single intervertebral level, the plate 12 will measure approximately 20 mm by 30 mm. The base plate 12 may take other shapes such as round or oval but, for purposes of the present description, will be shown and described as having a generally rectangular configuration. Preferably the plate is slightly curved or arcuate, as best seen in FIG. 4, along the axis which aligns with the axis of the spine. The curve is selected to conform to the natural lordotic curve of the cervical spine.

Apertures, shown as bores 24, 26, 28 and 30, are provided in the upper and lower portions of the plate adjacent each corner. The bores are for receipt of bone screws which will permanently affix the plate to the adjacent vertebrae as will be explained in greater detail below with respect to the surgical procedure.

Projecting from the rear surface 32 of the plate is an interbody graft 40. The interbody graft 40 is shown as being a generally rectangular structure although the graft may be in the form of other geometrical shapes such as circular, oval or wedge-shaped. The graft is located at an intermediate location extending from the rear of the plate. Upper and lower medial slots 50 and 52 extend in the plate from a location spaced several millimeters inward from the upper and lower edges of the plate, respectively, to locations adjacent the graft 40. Note the medial slots are elongate having a longitudinal dimension extending past bores 24, 26 and slot 52 extends past bores 28, 30.

The fusion implant can be fabricated from a variety of materials or combination of materials. The base plate 12 may be fabricated from a suitable metal such as titanium or stainless steel, a composite material such as carbon fiber or absorbable plastics which are approved for medical applications. The graft 40 may be an autograft or an alograft secured to the plate 12 by an adhesive or by a suitable fastener extending through the plate into the graft. However, it is preferred that the graft be partly or entirely a biosorbable interbody graft substantially a polymer or copolymer of glycolide, lactide, troxanone, trimethylene carbonates, lactones and the like. The term "bioabsorbable" generally refers to materials which facilitate and exhibit biologic elimination and degradation by the metabolism. Currently materials of this type, which are approved for medical use, include those materials known as PLA, PGA and PLGA. Materials of this type are commercially available and a representative material is the absorbable plastic produced by Macropore. Cervical plates made from titanium are currently available for such medical surgical supply houses such as Somaor Danek/Medtronic under the designation Atlantis and Zephyr.

As an alternative to fabricating the base or plate from one material and the graft from another, the entire structure may be a unitary structure fabricated from a single material such as the medical acceptable bioabsorable materials described above. The material must have the characteristics of being resorbable or bioresorbable and have the physical and structural characteristics to support the compressive loads of the vertebral column during the time fusion occurs. Such materials may lend themselves to various fabrication techniques such as injection molding or precision NC machining operations.

Figure 6:
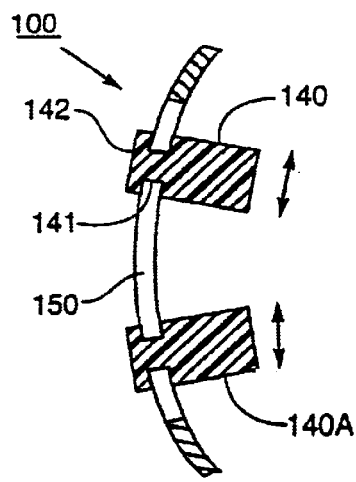
FIG. 6 is a cross-sectional view taken along line 6—6 of FIG. 5.
Figure 5A:
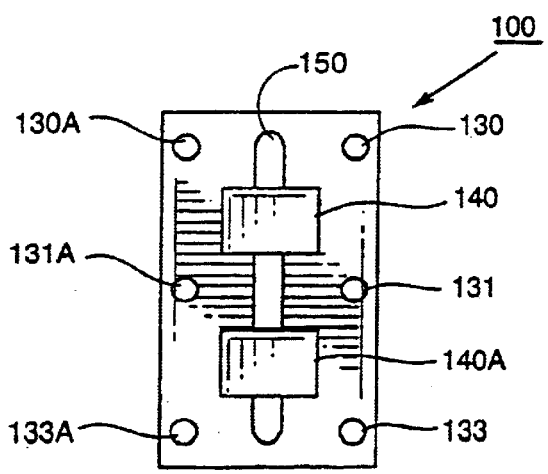
FIG. 5A is a front view of the implant shown in FIG. 5.
Figure 5:
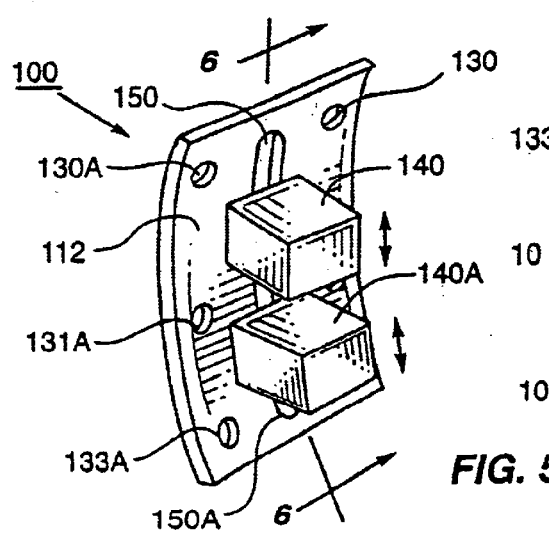
FIG. 5 is a front perspective view of another embodiment of the implant of the present invention having multiple grafts slidably positioned on the mounting plate.

Referring to FIGS. 5, 5A and 6, an alternate embodiment is shown which is generally designated by the numeral 100. In this embodiment, the fusion implant is intended for applications in which multiple vertebrae segments are to be fused using a single implant 100. The implant has a curved base or plate 112 which conforms to the curve of the spine and which has a longitudinal dimension which extends the required the length along the cervical spine in accordance with the medical procedure. The plate is provided with a pair of spaced-apart grafts 140, 140A slidable relative to the plate in medial slot 150. The grafts each have a projection 141 extending through the slot and secured at the rear of the plate by an enlarged retainer 142. The grafts 140, 140A, being slidable, can be aligned in the intervertebral spaces as required. Again, the plate and graft may be of various materials or a combination of materials as described above.

The plate 112 defines a plurality of bores 130, 130A, 131, 131A and 133, 133A. The upper bores 130, 130A, are adjacent the upper edges of the plate. Intermediate bores 131, 131A are located between the grafts 140, 140A and lower bores 133, 133A are adjacent the lower edge of the plate.

Figure 7:
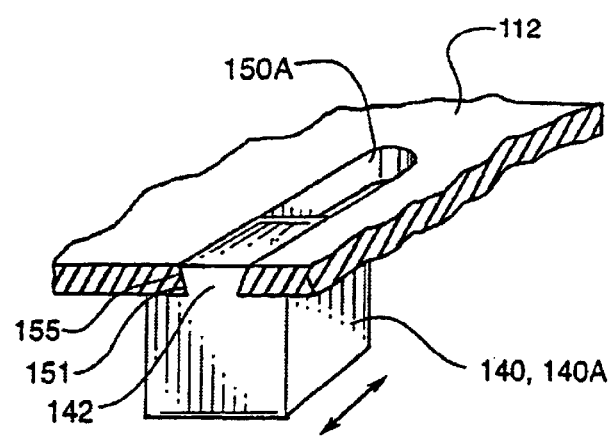
FIG. 7 is a detail view illustrating an alternate form of the slidable grafts shown in FIG. 5.

FIG. 7 shows another embodiment in which the grafts 140, 140A are slidable along slot 150A in plate 112. The slot has tapering sidewalls 155 which receive the projection 142 also having tapering sides which are captured in the slot to accommodate adjustment and prevent dislodgment. The advantage of the embodiment of FIG. 7 is that the retainer on the front of the plate, such as element 142 shown in FIG. 6, is eliminated leaving the rear of the plate free of projections.

Implant Procedure

The surgical insertion of the fusion implant into a space between adjacent vertebrae will be described and will assist in an understanding of the invention. Referring to FIGS. 8, 9 and 10, the insertion of infusion implant 10 (FIGS. 1 to 4) in an open surgical procedure in the cervical area is shown. The implant 10 is shown inserted between adjacent vertebrae V1 and V2 into the intervertebral space I. Normally a dissectomy is performed to remove all or a portion of the diseased disc in the areas. The implant 10 is then inserted into the position as shown in FIG. 8. Temporary retraction posts 80 are inserted into the upper and lower ends of the upper and lower medial compression slots 50, 52 as seen in FIG. 8. The retraction posts consist of two parts: an anchor screw 82 and a post 85. The anchor screw 82 has a threaded end 84 and an opposite end 86 which is hollow and is internally threaded. The head is slotted at 88 to accommodate a tool such as a screwdriver. The head is wider than the width of the medial compression slots 50, 52 to retain the plate. The anchor screw 82 is inserted through slot 50 and is secured in place in a hole bored in the upper vertebrae V1. Another anchor screw is inserted into the slot aligned with the lower end of the lower compression slot. An anchor post 85 is then aligned with the threaded female end of each of the anchor screws 82 and secured by rotating the post so that the male threaded end 87 engages the female bore in the anchor screw. When this is completed, the fusion implant is positioned as shown in FIG. 8.

As mentioned above, according to Wolf's law, in the natural healing process, bone growth replacement is stimulated by application of force. The stimulating force is applied by compressing the adjacent vertebrae V1 and V2 using a suitable compression tool T as shown in FIG. 8. Further, force will be directly applied to the interspace after absorption of the plate. The compression tool T has jaws which will engage the spaced-apart temporary posts 80. When the required compression force has been applied, the posts are temporarily maintained in the desired position by the tool T and permanent screws 90 are inserted into the bores 24, 26, 28 and 30 in the plate and into the bone. Guide or pilot holes may be first drilled in the vertebrae V1 and V2 and the screws inserted and tightened as shown in FIG. 7. Once all of the screws are in position, the vertebra are now held in the compressed condition by the screws and the tool T may be released. Once the tool T is released, the anchor posts 80 may be unscrewed and the temporary compression screws may also be removed leaving the implant in place.

This same basic procedure is performed using the alternate embodiments as shown in FIGS. 5 to 7, which embodiments are intended for use for fusing multiple vertebral segments. With these embodiments, the medial slots 150, 150A allow axial adjustment of the grafts and the same slots will also serve to accommodate insertion and removal of the temporary compression posts.

From the foregoing, it will be seen that the present invention provides a fusion implant having a slotted plate which allows compression. A graft, which may be natural or synthetic graft, is affixed to the plate and the cervical plate and alograft may be molded or formed as a single, absorbable plastic member. With the present system, rigidly affixing the graft to the plate eliminates the need to mortise the graft thus preserving more of the cervical bone for fusion minimizing the size of the space needed to undergo fusion and protect the spinal cord against injury by minimizing the risk of graft dislodgement.

The absorbable fixation leads to mechanical loading of the fusion mass preventing osteoporosis. The compression slots facilitate close approximation of the vertebral bodies to the alograft surface enhancing and promoting fusion. Retraction posts with anchors provide tissue retraction with minimal risks to adjacent structures such as the carotid arteries, esophagus and recurrent laryngeal nerve.

It will be obvious to those skilled in the art to make various changes, alterations and modifications to the invention described herein. To the extent such changes, alterations and modifications do not depart from the spirit and scope of the appended claims, they are intended to be encompassed therein.

I claim:

1. An implant device for fusion of adjacent first and second vertebrae having an intervertebral space therebetween, said device comprising:
   (a) a rigid baseplate;
   (b) said plate defining a first aperture alignable with said first vertebra and a second aperture alignable with said second vertebra;
   (c) a graft integrally attached to said plate alignable with said intervertebral space; and
   (d) said plate defining elongate first and second axially aligned slots disposed on opposite sides of said graft, said first slot alignable with said first vertebra and said second slot alignable with said second vertebra whereby said first and second vertebrae can be temporarily compressed by a compression tool via said slots and thereafter said plate may be affixed by fasteners extending through said first and second apertures into said vertebrae with said graft compressed.

2. The implant device of claim 1 wherein said slots are centrally positioned with respect to said plate.

3. The implant device of claim 1 wherein said graft is selected from the group consisting of alografts, autografts and synthetic grafts.

4. The implant device of claim 1 wherein said graft is a bioabsorbable material.

5. The implant device of claim 1 wherein said device is integrally formed from a bioabsorbable material.

6. The implant device of claim 5 wherein said material is selected from the group consisting of PLA, PGA and PLGA.

7. The implant device of claim 1 wherein said plate is curved to conform to the curvature of the spine.

8. An implant device for fusing adjacent first and second cervical vertebrae having an intervertebral space therebetween, said device comprising:
   (a) a generally rectangular rigid baseplate having opposite first and second sides and opposite first and second ends;
   (b) said plate defining at least one first bore adjacent said first end and at least one second bore adjacent said second end, said at least one first bore alignable with said first vertebra and said at least one second bore alignable with said second vertebra;
   (c) a graft extending from the second side said plate at an intermediate location and affixed thereto;
   (d) said plate defining a first elongate slot extending from a location above said graft toward the top end of said plate to a location aligned with said first vertebrae; and
   (e) said plate defining a second elongate slot aligned with the first slot and extending from adjacent the graft toward said bottom end of the plate to a location aligned with said second vertebrae whereby said first and second vertebrae can be temporarily compressed by a compression tool via said slots and thereafter said plate may be affixed by fasteners extending through said bores with said graft compressed.

9. The implant device of claim 8 wherein said graft is selected from the group consisting of alografts, autografts and synthetic grafts.

10. The implant device of claim 8 wherein said plate is curved to conform to the curvature of the spine.

11. The implant device of claim 8 wherein said plate and graft are integrally formed from a bioabsorbable material.

12. The implant device of claim 8 wherein said graft is substantially rectilinear in cross section.

13. The implant device of claim 8 having multiple first and second bores.

14. A spinal fusion procedure for fusing adjacent vertebrae sections separated by a disc comprising:

(a) performing a dissectomy to remove any diseased disc areas;

(b) providing an implant device having a plate with apertures and first and second aligned slots having a graft thereon;

(c) inserting the graft into the intervertebral disc area;

(d) inserting a first temporary anchor pin through said first slot and a second temporary anchor pin through said second slot and temporarily securing the said anchors to said first and second vertebrae;

(e) applying a compressive force to said anchor pins to compress the graft;

(f) maintaining said compressive force while inserting fasteners through said apertures to permanently affix said plate to the vertebrae;

(g) releasing the compressive force; and (h) removing the temporary anchor pins.

15. A spinal implant device comprising:

(a) a baseplate defining an elongate slot;

(b) said plate defining apertures alignable with selected spinal vertebrae for receiving fasteners; and (c) first and second grafts slidably engaged in said slot and independently slidable along said slot and alignable with separate selected intervertebral areas.

16. The device of claim 15 wherein said slot is a medial slot and said grafts have projections extending into said slot with retainer means associated therewith.

* * * * *